United States Patent [19]

Shimizu et al.

[11] Patent Number: 5,624,601
[45] Date of Patent: Apr. 29, 1997

[54] SILACYCLOHEXANE COMPOUNDS, A LIQUID CRYSTAL COMPOSITION COMPRISING THE SAME AND A LIQUID CRYSTAL DEVICE COMPRISING THE COMPOSITION

[75] Inventors: Takaaki Shimizu; Takeshi Kinsho; Tsutomu Ogihara; Tatsushi Kaneko; Mutsuo Nakashima, all of Niigata-ken; Hideshi Kurihara, Kawasaki, all of Japan

[73] Assignee: Shin-Etsu Chemical Co., Ltd., Tokyo, Japan

[21] Appl. No.: 546,254

[22] Filed: Oct. 20, 1995

[30] Foreign Application Priority Data

Oct. 20, 1994 [JP] Japan .................. 6-282739
Nov. 10, 1994 [JP] Japan .................. 6-301328

[51] Int. Cl.$^6$ .................. C09K 19/34; C09K 19/30; C07F 7/08
[52] U.S. Cl. .................. 252/299.61; 556/406
[58] Field of Search .................. 252/299.61, 299.63; 556/406

[56] References Cited

U.S. PATENT DOCUMENTS

| | | | |
|---|---|---|---|
| 4,496,501 | 1/1985 | Shimizu et al. | 252/299.61 |
| 5,454,977 | 10/1995 | Shimizu et al. | 252/299.61 |
| 5,498,737 | 3/1996 | Ogihara et al. | 556/406 |

FOREIGN PATENT DOCUMENTS

| | | |
|---|---|---|
| 0003215 | 11/1978 | European Pat. Off. . |
| 0355008 | 8/1989 | European Pat. Off. . |
| 0665232 | 1/1995 | European Pat. Off. . |
| 60-17777 | 5/1985 | Japan . |
| 61-24382 | 6/1986 | Japan . |
| 63-53178 | 10/1988 | Japan . |
| 142261 | 9/1989 | Japan . |
| 247455 | 10/1990 | Japan . |
| 251893 | 11/1990 | Japan . |
| 256343 | 11/1990 | Japan . |

OTHER PUBLICATIONS

"Acetolysis of 4,4-Disubstituted 4-Silacyclohexyl Tosylates: Effect of Remote Silicon Substitution on Organic Reactivity" by Stephen S. Washburne et al; Journal of Organometallic Chemistry, 133 (1977) pp., 7-17.

"Preparation and Spectral Properties of β-Silyl-Substituted α,β-Unsaturated Ketones" by Raymond A. Felix et al; J. Org. Chem., vol. 37, No. 14, 1972; pp., 2323-2327.

"Oxidations in Organic Chemistry" by Milos Hudlicky; pp. 106, 107, 130, 131, 176-181.

"Protective Groups in Organic Synthesis" by Theodora W. Greene; John Wiley & Sons, Inc., 1981; pp. 12-151.

*Primary Examiner*—Cynthia Harris Kelly
*Attorney, Agent, or Firm*—Lowe, Price, LeBlanc & Becker

[57] ABSTRACT

A silacyclohexane compound of the following formula (I)

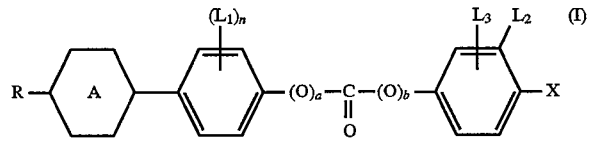

wherein R represents an organic residue;

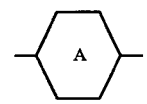

represents a trans-1-sila-1,4-cyclohexylene group or trans-4-sila-1,4-cyclohexylene group having a substituent of H, F, Cl or $CH_3$; $L_1$ represents F, $L_2$ and $L_3$ independently represent H, F, Cl or $CH_3$; X represents an organic residue, F or Cl; and n is an integer of 0, 1, or 2 and a and b are, respectively, 0 or 1 provided that a+b=1. Silacyclohexane compounds are useful in liquid crystal compositions and also in liquid crystal devices.

11 Claims, No Drawings

SILACYCLOHEXANE COMPOUNDS, A LIQUID CRYSTAL COMPOSITION COMPRISING THE SAME AND A LIQUID CRYSTAL DEVICE COMPRISING THE COMPOSITION

BACKGROUND OF THE INVENTION

1. Field of the Invention

This invention relates to novel silacyclohexane compounds and also to liquid crystal compositions comprising the compounds and devices comprising the compositions.

2. Description of the Prior Art

The liquid crystal display devices make use of optical anisotropy and dielectric anisotropy of liquid crystal substances. Depending on the mode of display, a variety of display systems are known including those of a twisted nematic type (TN type), a supertwisted nematic type (STN type), a super birefringence type (SBE type), a dynamic scattering type (DS type), a guest/host type, a type of deformation of aligned phase (DAP type), and an optical mode interference type (OMI type). The most popular display device is one which is based on the Schadt-Helfrich effect and has a twisted nematic structure.

Although the properties of the liquid crystal substances used in these liquid crystal devices depend, more or less, on the type of display, it is commonly required that the liquid crystal substances have a wide range of temperatures at which they are able to work as a liquid crystal and that they be stable against moisture, air, light, heat, electric field and the like. Moreover, the liquid crystal substances should desirably be low in viscosity and should ensure a short address time, a low threshold voltage and a high contrast in cells.

Liquid substances which can satisfy all these requirements have never been known when used singly. In practice, several to ten and several liquid compounds or latent liquid crystal compounds are mixed and used in the form of a mixture. To this end, it is important that constituent components be readily compatible with one another.

Typical of such constituent components are ester compounds having a relatively high nematic-isotropic transition temperature, $T_{NI}$. The ester compounds include those compounds having phenyl ester structures of cyclohexylbenzoic acid of the following formulas.

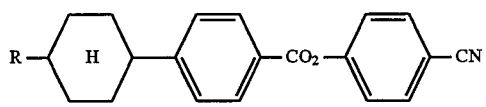

(1)

wherein R represents an alkyl group having from 1 to 8 carbon atoms as set forth in Japanese Patent Publication No. 60-17777.

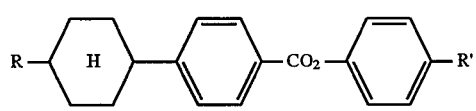

(2)

wherein R and R' independently represent an alkyl group having from 1 to 8 carbon atoms as set forth in Japanese Patent Publication No. 60-17777.

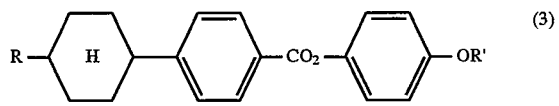

(3)

wherein R and R' independently represent an alkyl group having from 1 to 8 carbon atoms as set forth in Japanese Patent Publication No. 60-17777.

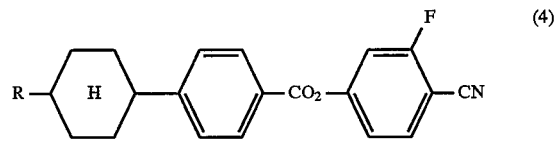

(4)

wherein R represents an alkyl group having from 1 to 9 carbon atoms as set forth in Japanese Patent Publication No. 61-24382.

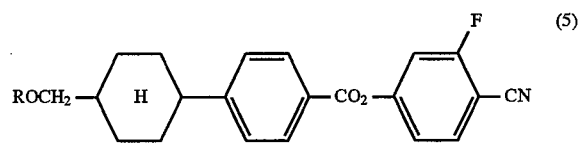

(5)

wherein R represents an alkyl group having from 1 to 10 carbon atoms as set out, for example, in Japanese Patent Publication No. 1-42261.

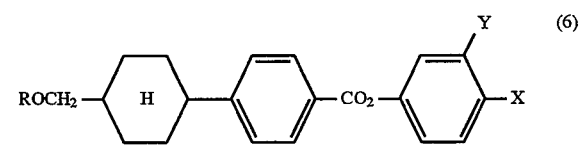

(6)

wherein R represents an alkyl group having from 1 to 10 carbon atoms and X and Y independently represent F or Cl as set out in Japanese Patent Publication No. 2-51893.

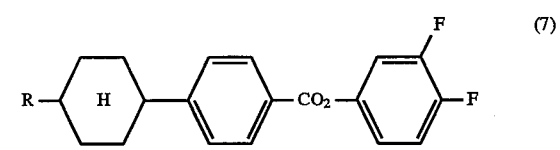

(7)

wherein R is an alkyl group having from 1 to 9 carbon atoms as set out in Japanese Patent Publication No. 2-56343.

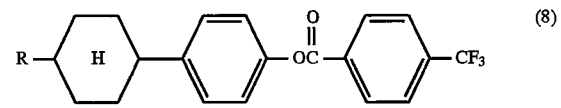

(8)

wherein R is an alkyl group having from 1 to 10 carbon atoms as set out in Japanese Patent Publication No. 2-47455.

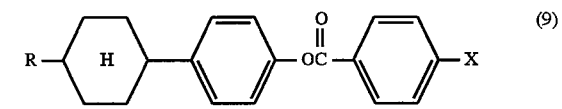

(9)

wherein R is an alkyl group having from 1 to 10 carbon atoms and X is F or Cl as set out in Japanese Patent Publication No. 63-53178.

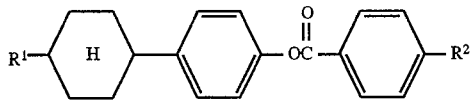

wherein R¹ represents an alkyl group having from 1 to 8 carbon atoms, and R² represents R, RO or CN in which R is an alkyl group having from 1 to 8 carbon atoms as set out in Japanese Patent Publication No. 60-17777.

As the liquid crystal display devices recently have wider utility, the characteristic properties required for the liquid crystal materials become severer along with a diversity of drive systems and working modes being in progress. In particular, liquid crystal materials should have a high response speed and, for on-vehicle needs, should have a nematic phase extended to a high temperature region from the standpoint of use conditions. For the extension of the nematic phase to a high temperature region, it is sufficient to add a liquid crystal compound having a high nematic-isotropic transition temperature, $T_{NI}$, as a constituent component. Known components having a high $T_{NI}$ value include, for example, 4,4"-substituted terphenyl, 4,4'-substituted biphenylcyclohexane and 4,4'-substituted cyclohexylbiphenylcyclohexane. However, these compounds because the viscosity of mixed liquid crystal to increase, thus bringing about a response speed being lowered.

SUMMARY OF THE INVENTION

It is an object of the invention to provide novel compounds serving as a liquid crystal substance which have a relatively high nematic-isotropic transition temperature, $T_{NI}$, and does not increase the viscosity of a mixed liquid crystal composition comprising the compound.

It is another object of the invention to provide a novel liquid crystal compound which has such a structure as having never been known in the art and has a silacyclohexane ring containing a silicon atom in the molecule.

It is a further object of the invention to provide a liquid crystal composition which comprise at least one compound of the type as set out above and also a liquid crystal display device comprising the composition.

The above object can be achieved, according to one embodiment of the invention, by a silacyclohexane compound of the following formula (I)

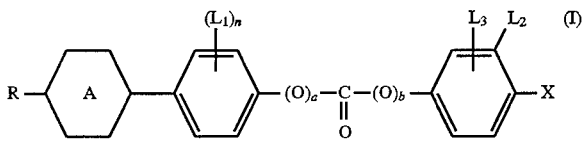

wherein R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms or an alkenyl group having from 2 to 8 carbon atoms;

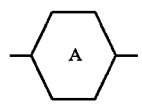

represents a trans-1-sila-1,4-cyclohexylene group or trans-4-sila-1,4-cyclohexylene group in which the silicon atom at the 1 or 4 position has a substituent of H, F, Cl or $CH_3$; $L_1$ represents F, $L_2$ and $L_3$ independently represent H, F, Cl or $CH_3$; X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_iCY=CX_1X_2$ wherein 1 is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl; and n is an integer of 0, 1, or 2 and a and b are, respectively, 0 or 1 provided that a+b=1.

The compounds of the formula (I) include compounds of the formulas (II) and (III)

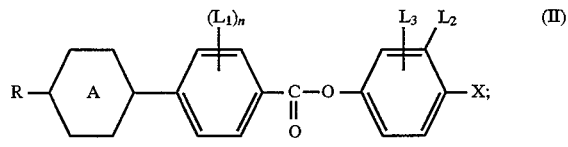

and

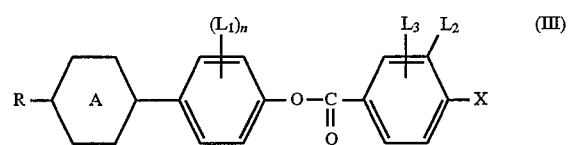

The invention also provides a liquid crystal composition which comprises the silacyclohexane compound of the formula (I). Preferably, the silacyclohexane compound is present in amounts of from 5 to 30 wt % of the composition. Furthermore, the invention provides a liquid crystal display device comprising the liquid crystal composition.

Among the compounds of the formula (I) according to the invention, those compounds of the formula (I) wherein X is an alkyl group or an alkoxy group are low in polarity. When these compounds are employed as a constituent component in liquid crystal compositions, the $T_{NI}$ value increases and these tricyclic compounds do not increase a viscosity of the composition on comparison with the afore-mentioned tetracyclic compounds used as the high $T_{NI}$ component. With the compounds of the formula (I) wherein X is a group other than those groups mentioned above, they have an effect of increasing the $T_{NI}$ value and have a dielectric anisotropy (Δε) which is either positive or negative. As a result, the compounds serve to lower the drive voltage and ensure a high response speed.

DETAILED DESCRIPTION OF THE INVENTION

The novel compounds of the invention serving as a liquid crystal substance are those of the formula (I) indicated hereinbefore. More specifically, the compounds have novel ring structures including a trans-1-silacyclohexane ring or a trans-4-silacyclohexane ring and include, for example, the compounds of the following formulas (IV) to (VII):

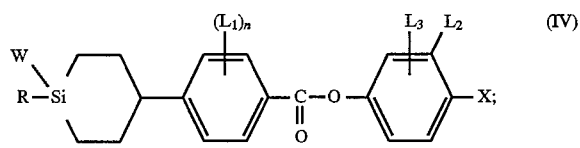

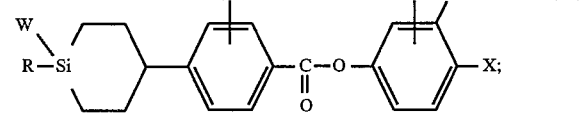

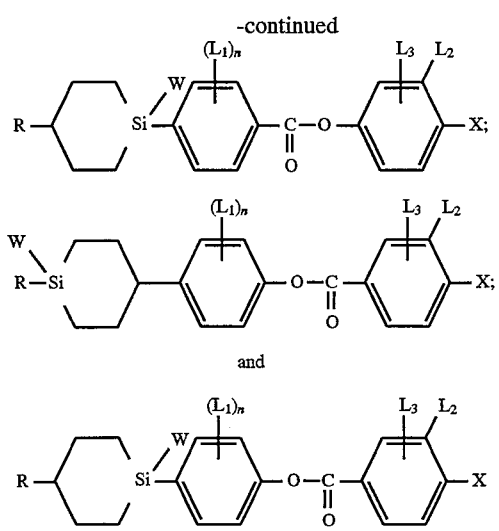

In the formulas (IV) to (VII), R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms or an alkenyl group having from 2 to 8 carbon atoms, X represent a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_iCY=CX_1X_2$ wherein i is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl, W represents H, F, Cl or $CH_3$, $L_1$ is F, $L_2$ and $L_3$ independently represent H, F, Cl or $CH_3$, and n is 0, 1 or 2.

Specific examples of the linear alkyl group having from 1 to 10 carbon represented by R include methyl, ethyl, n-propyl, n-butyl, n-pentyl, n-hexyl, n-heptyl, n-octyl, n-nonyl and n-decyl.

Specific examples of the branched alkyl group having 3 to 8 carbon atoms represented by R include isopropyl, 1-methylpropyl, 2-methylpropyl, sec-butyl, isobutyl, 1-methylbutyl, 2-methylbutyl, 3-methylbutyl, 1-methylpentyl, 2-methylpentyl, 3-methylpentyl, 1-ethylpentyl, 1-methylhexyl, 2-methylhexyl, 3-methylhexyl, 2-ethylhexyl, 3-ethylhexyl, 1-methylheptyl, 2-methylheptyl and 3-methylheptyl.

Specific examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl and ethoxypentyl.

Specific examples of the mono or difluoroalkyl group having from 1 to 10 carbon atoms include fluoromethyl, 1-fluoroethyl, 1-fluoropropyl, 1-fluorobutyl, 1-fluoropentyl, 1-fluorohexyl, 1-fluoroheptyl, 1-fluorooctyl, 1-fluorononyl, 1-fluorodecyl, 2-fluoroethyl, 2-fluoropropyl, 2-fluorobutyl, 2-fluoropentyl, 2-fluorohexyl, 2-fluoroheptyl, 2-fluorooctyl, 2-fluorononyl, 2-fluorodecyl, 3-fluoropropyl, 3-fluorobutyl, 3-fluoropentyl, 3-fluorohexyl, 3-fluoroheptyl, 3-fluorooctyl, 3-fluorononyl, 3-fluorodecyl, 4-fluorobutyl, 4-fluoropentyl, 4-fluorohexyl, 4-fluoroheptyl, 4-fluorooctyl, 4-fluorononyl, 4-fluorodecyl, 5-fluoropentyl, 5-fluorohexyl, 5-fluoroheptyl, 5-fluorooctyl, 5-fluorononyl, 5-fluorodecyl, 6-fluorohexyl, 6-fluoroheptyl, 6-fluorononyl, 6-fluorodecyl, 7-fluoroheptyl, 7-fluorooctyl, 7-fluorononyl, 7-fluorodecyl, 8-fluorooctyl, 8-fluorononyl, 8-fluorodecyl, 9-fluorononyl, 9-fluorodecyl, 10-fluorodecyl, difluoromethyl, 1,1-difluoroethyl, 1,1-difluoropropyl, 1,1-difluorobutyl, 1,1-difluoropentyl, 1,1-difluorohexyl, 1,1-difluoroheptyl, 1,1-difluorooctyl, 1,1-difluorononyl, 1,1-difluorodecyl, 2,2-difluoroethyl, 2,2-difluoropropyl, 2,2-difluorobutyl, 2,2-difluoropentyl, 2,2-difluorohexyl, 2,2-difluoroheptyl, 2,2-difluorooctyl, 2,2-difluorononyl, 2,2-difluorodecyl, 3,3-difluoropropyl, 3,3-difluorobutyl, 3,3-difluoropentyl, 3,3-difluorohexyl, 3,3-difluoroheptyl, 3,3-difluorooctyl, 3,3-difluorononyl, 3,3-difluorodecyl, 4,4-difluorobutyl, 4,4-difluoropentyl, 4,4-difluorohexyl, 4,4-difluoroheptyl, 4,4-difluorooctyl, 4,4-difluorononyl, 4,4-difluorodecyl, 5,5-difluoropentyl, 5,5-diflourohexyl, 5,5-difluoroheptyl, 5,5-difluorooctyl, 5,5-difluorononyl, 5,5-difluorodecyl, 6,6-difluorohexyl, 6,6-difluoroheptyl, 6,6-difluorooctyl, 6,6-difluorononyl, 6,6-difluorodecyl, 7,7-difluoroheptyl, 7,7-difluorooctyl, 7,7-difluorononyl, 7,7-difluorodecyl, 8,8-difluorooctyl, 8,8-difluorononyl, 8,8-difluorodecyl, 9,9-difluorononyl, 9,9-difluorodecyl and 10,10-difluorodecyl.

Specific examples of the alkenyl group having from 2 to 8 carbon atoms include vinyl, 1-propenyl, allyl, 1-butenyl, 3-butenyl, isoprenyl, 1pentenyl, 3-pentenyl, 4-pentenyl, dimethylallyl, 1-hexenyl, 3-hexenyl, 5-hexenyl, 1-heptenyl, 3-heptenyl, 6-heptenyl and 7-octenyl.

Examples of the linear alkyl group represented by X are those indicated above with respect to R. Examples of the linear alkoxy group having from 1 to 10 carbon atoms represented by X include methoxy, ethoxy, n-propoxy, n-butoxy, n-pentoxy, n-hexyloxy, n-heptyloxy, n-octyloxy, n-nonyloxy and n-decyloxy. Examples of the alkoxyalkyl group having from 2 to 7 carbon atoms include methoxymethyl, ethoxymethyl, propoxymethyl, butoxymethyl, pentoxymethyl, hexyloxymethyl, methoxyethyl, ethoxyethyl, propoxyethyl, butoxyethyl, pentoxyethyl, methoxypropyl, ethoxypropyl, propoxypropyl, butoxypropyl, methoxybutyl, ethoxybutyl, propoxybutyl, methoxypentyl, ethoxypentyl and methoxyhexyl.

The silacyclohexane compound of the formula (I) has a moiety of the following formula (1)

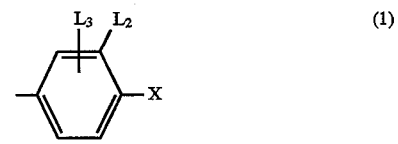

Specific examples of the moiety include residues of the following formulas

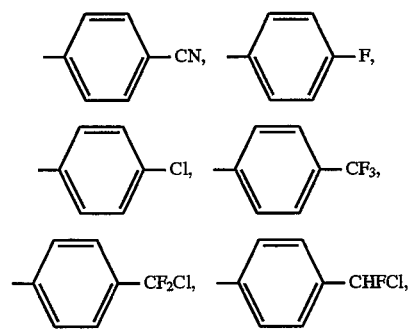

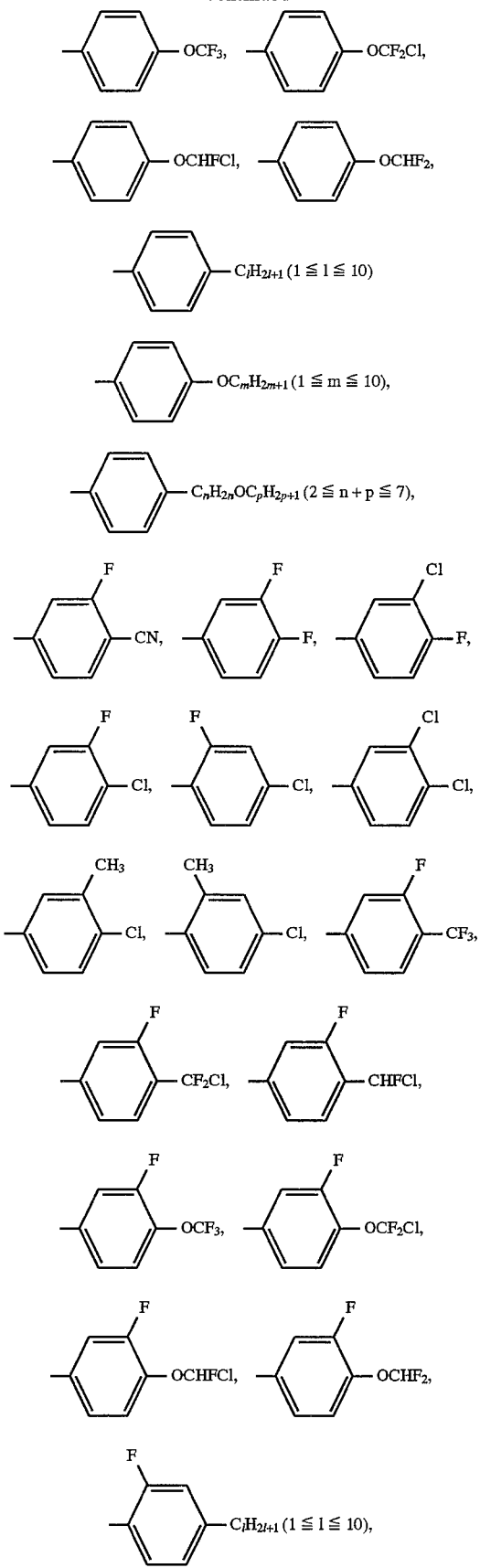
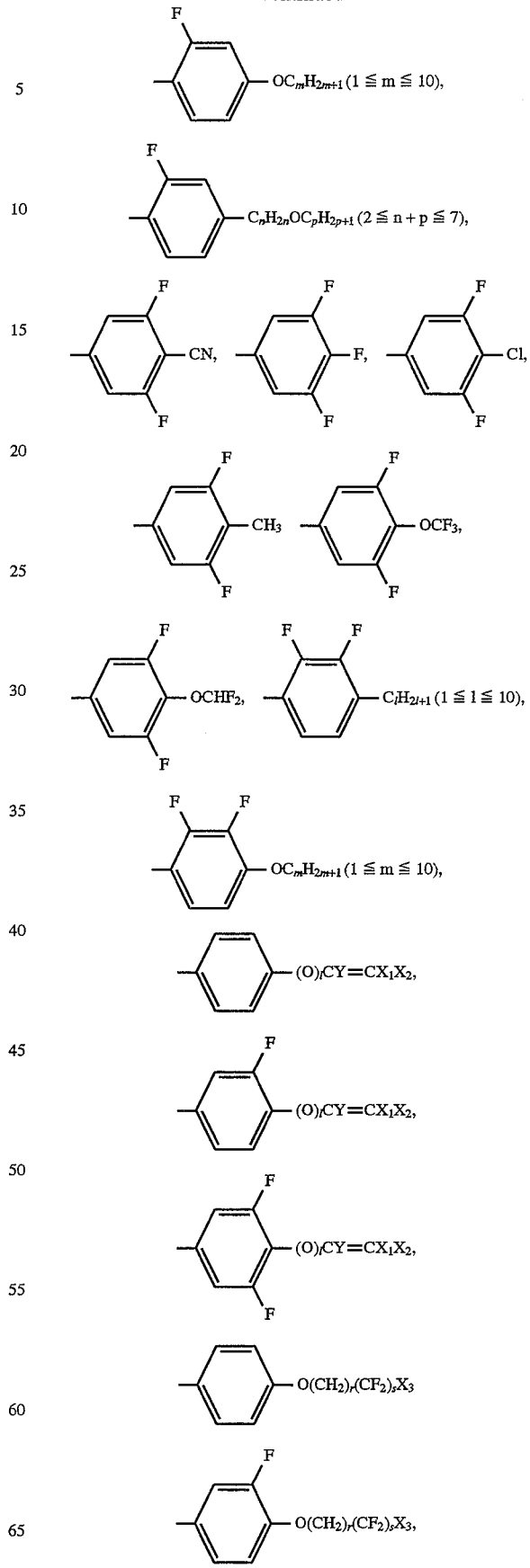

-continued and

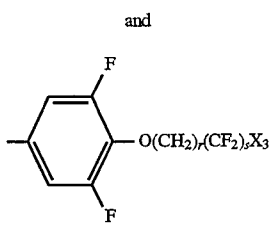

wherein Y, $X_1$, $X_2$, $X_3$, l, r and s are, respectively, as defined hereinbefore.

Preferred silacyclohexane compounds include those of the afore-indicated formulas (IV) and (VI) shown below:

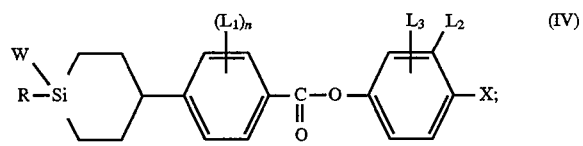

and

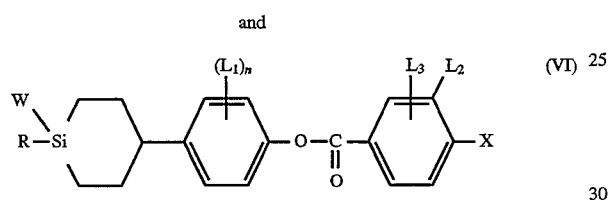

Preferred groups represented by R include: linear alkyl groups having from 2 to 7 carbon atoms, e.g. ethyl, n-propyl, n-butyl, n-pentyl, n-hexyl and n-heptyl; mono or difluoroalkyl groups having from 2 to 7 carbon atoms, such as 2-fluoroethyl, 2-fluoropropyl, 2-fluorobutyl, 2-fluoropentyl, 2-fluorohexyl, 2-fluoroheptyl, 4-fluorobutyl, 4-fluoropentyl, 4-fluorohexyl, 4-fluoroheptyl, 5-fluorohexyl, 5-fluoroheptyl, 6-fluorohexyl, 6-fluoroheptyl, 7-fluoroheptyl, 2,2-difluoroethyl, 2,2-difluoropropyl, 2,2-difluorobutyl, 2,2-difluoropentyl, 2,2-difluorohexyl, 2,2-difluoroheptyl, 4,4-difluorobutyl, 4,4-difluoropentyl, 4,4-difluorohexyl, 4,4-difluoroheptyl, 5,5-difluoropentyl, 5,5-difluorohexyl, 5,5-difluoroheptyl, 6,6-difluorohexyl, 6,6-difluoroheptyl and 7,7-difluoroheptyl; branched alkyl groups having from 3 to 8 carbon atoms, such as isopropyl, 1-methylpropyl, 2-methylpropyl, 1-methylbutyl, 2-methylbutyl, 3-methylbutyl, 1-methylpentyl, 2-methylpentyl and 2-ethylhexyl; alkoxyalkyl groups having from 2 to 6 carbon atoms, such as methoxymethyl, methoxyethyl, methoxypropyl, methoxypentyl, ethoxymethyl, ethoxyethyl, propoxymethyl and pentoxymethyl; and alkenyl groups having from 2 to 8 carbon atoms, such as vinyl group, 1-propenyl group, 3-butenyl group, 1-pentenyl group, 3-pentenyl group, 4-pentenyl group, 1-hexenyl group, 5-hexenyl group, 6-heptenyl group and 7-octenyl group.

Preferred atoms or groups represented by W include H, F or $CH_3$.

Preferred moieties represented by the formula (1)

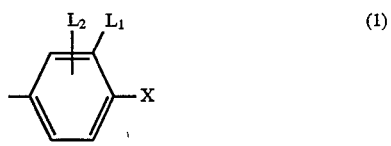

are those indicated below

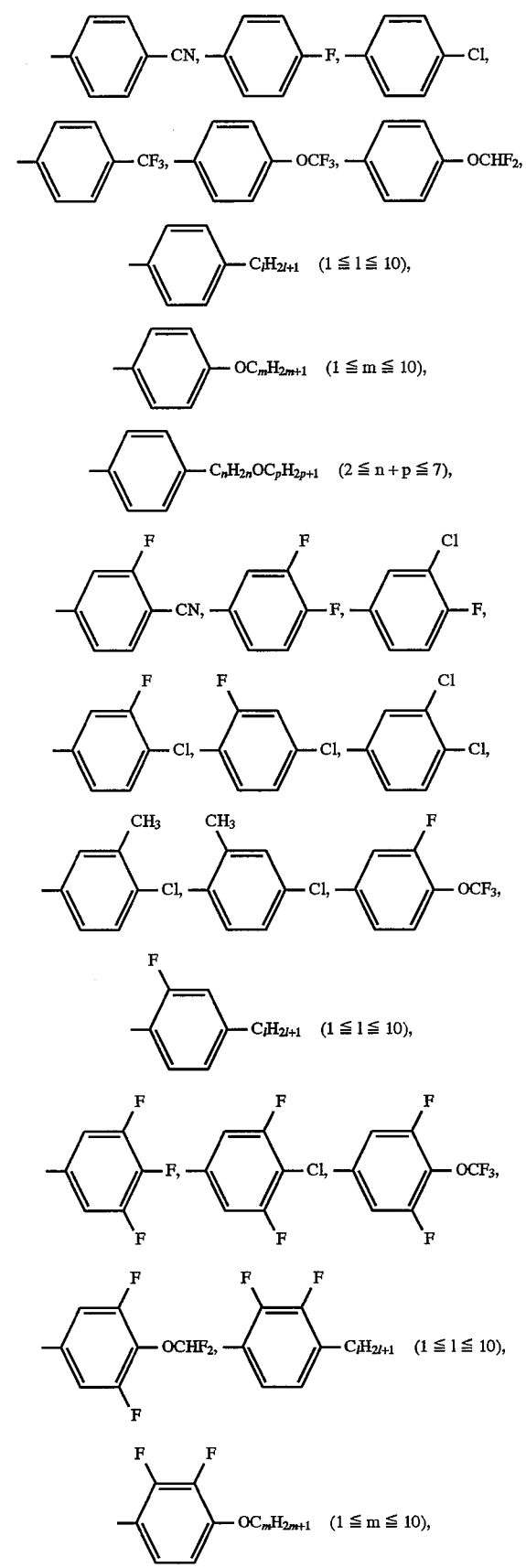

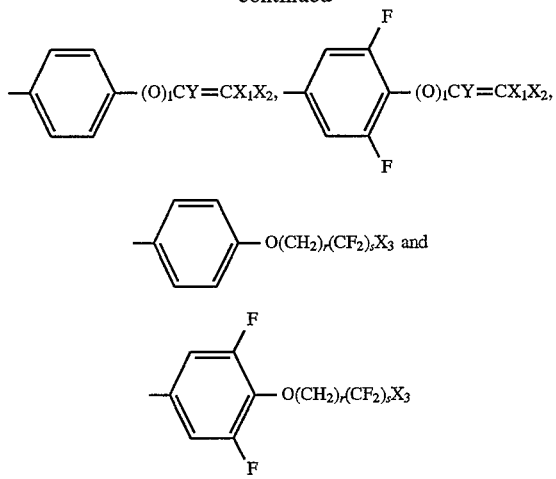

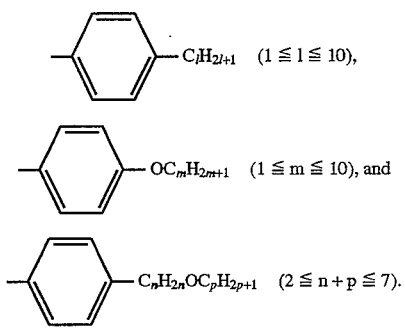

Of these, the compounds having the moieties of the following formulas exhibit a value of $\Delta\epsilon$ close to zero

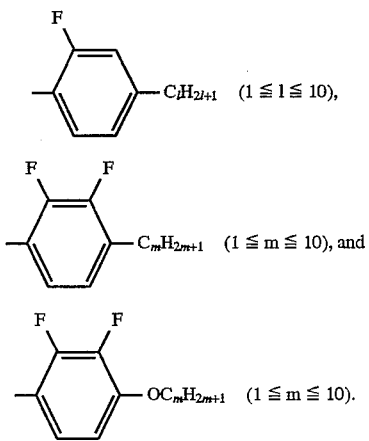

Moreover, the compounds having moieties of the following formulas exhibit a negative value of $\Delta\epsilon$ These compounds are suitable for use in DS-type, DAP-type and GH-type display devices.

The preparation of the silacyclohexane compound of the formula (I) according to the invention is now described. The silacyclohexane compounds of the formula (I) differ in manner of preparation depending on the type of substituent joined to the silicon atom of the silacyclohexane ring.

With the methylsilacyclohexane compounds of the following formulas (IV) to (VII) wherein the substituent bonded to the silicon atom of the silacyclohexane ring is a methyl group, i.e. W is a methyl group in the formulas,

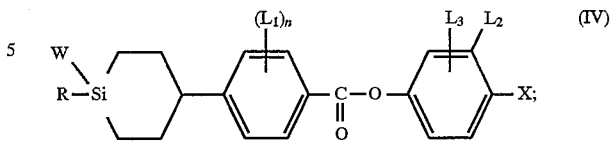

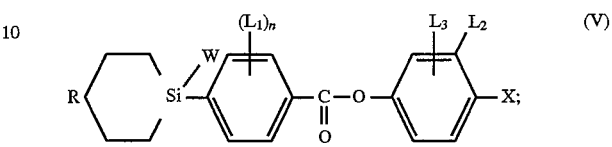

a carboxylic acid of the general formula (2) or (3)

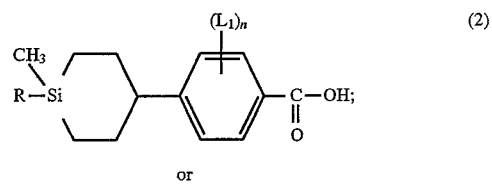

or

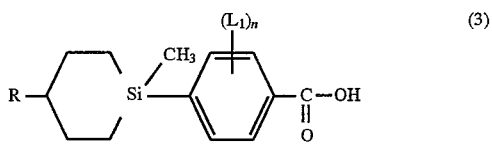

is reacted with a phenol compound of the following general formula (4) through esterification or through dehydration and condensation

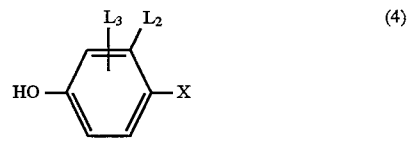

wherein X, $L_2$ and $L_3$ have, respectively, the same meanings as defined hereinbefore.

The esterification reactions include (1) a method wherein the two compounds are condensed by use of dehydrators and (2) a method wherein the carboxylic acid is first converted to an acid chloride and then reacted with the phenol compound in the presence of bases.

The dehydrators used in the method (1) include, for example, diimides such as N,N'-dicyclohexylcarbodiimide, acid anhydrides such as trifluoroacetic anhydride, carbonyldiimidazole, 2-chloropyridinium salts, 3-chloroisooxazolium salts, and combinations of 2,2'-dipyridyldisulfide and phosphines such as methyl phosphine.

In this case, the reaction is preferably effected under conditions of a temperature of from 0° to 100° C. for a time of from 0.5 to 10 hours in a solvent inert to the reaction. Examples of the solvent include carbon tetrachloride, methylene chloride, aromatic hydrocarbons such as benzene, toluene, xylene and the like, and ethers such as tetrahydrofuran.

The reagents used to convert the carboxylic acid to a corresponding acid chloride in the method (2) include thionyl chloride, phosphorus pentachloride, oxalyl chloride, and combinations of carbon tetrachloride and phosphines. This reaction proceeds by a usual manner preferably under conditions of a temperature ranging from 0° to 100° C. The acid chloride is then reacted with the phenol compound in the presence of bases. Examples of the base include pyridine, 4-dimethylaminopyridine, N,N-dimethylaniline, triethylamine, tetramethylurea and the like. This reaction proceeds readily under normal temperature and pressure conditions.

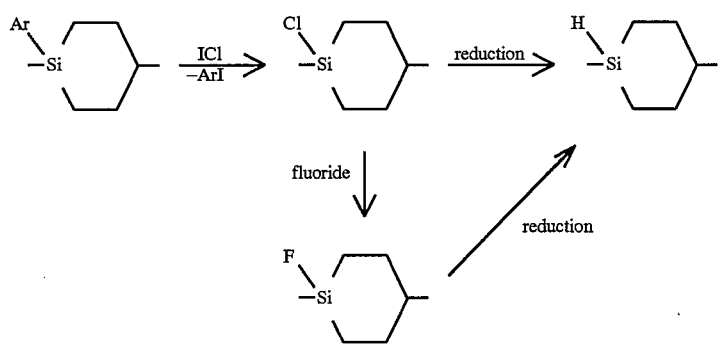

Next, the compounds of the formulas (IV) and (V) wherein W is chlorine, fluorine or hydrogen, (i.e. the atom or substituent joined to the silicon atom or atoms of the silacyclohexane ring or rings is chlorine, fluorine or hydrogen), include chlorosilacyclohexane, fluorosilacylohexane and hydrosilacyclohexane compounds. For the preparation of these compounds, arylsilacyclohexane compounds wherein an aryl group such as phenyl or tolyl is attached to the silicon atom of the silacyclohexane ring is used as an intermediate for preparing the chlorosilacyclohexane, fluorosilacylohexane and hydrosilacyclohexane compounds. The arylsilacyclohexane compounds are those compounds of the general formula (IV) and (V) wherein W is an aryl group such as phenyl or tolyl.

These arylsilacyclohexane intermediate compounds are prepared through esterification or through dehydration and condensation between corresponding carboxylic acids of the following general formula (5) or (6)

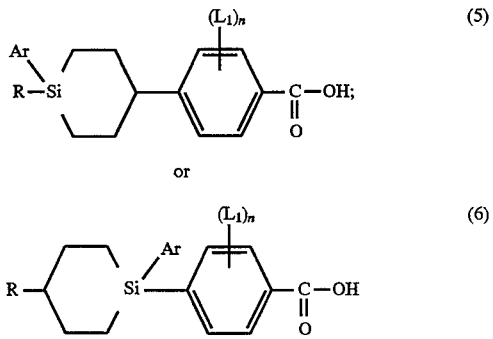

wherein Ar is phenyl or tolyl, and phenol compounds of the afore-indicated general formula (4), like the compounds of the formulas (IV) and (V) wherein W is CH$_3$

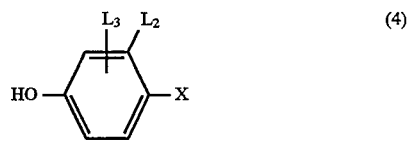

wherein X, L$_2$ and L$_3$ have, respectively, the same meanings as defined hereinbefore.

The conversion of the arylsilacyclohexane intermediate compound to an intended chlorosilacyclohexane, fluorosilacylohexane or hydrosilacyclohexane compound is carried out according to the following reaction sequence wherein only the moiety taking part in the conversion reaction is shown wherein Ar represents phenyl or tolyl.

As will be apparent from the above reaction sequence, when iodine monochloride is reacted with the arylsilacyclohexane compound, a chlorosilacyclohexane compound is obtained through the halo de-silylation reaction. The de-silylation reaction may be caused in a wide range of temperatures. Preferably, the temperature used is in the range of from 0° to 80° C., more preferably from 10° to 40° C.

When the resultant chlorosilacyclohexane compound is reacted with fluorides such as cesium fluoride, copper (I) fluoride, antimony fluoride, zinc fluoride, calcium fluoride, tetra-n-butylammonium fluoride and the like, a fluorosilacyclohexane compound of the formulas (IV) and (V) wherein W is fluorine. The reaction is carried out at a temperature ranging from 0 to the boiling point of the reaction system in a hydrocarbon solvent such as hexane, heptane, benzene, toluene or the like.

When the chlorosilacyclohexane or fluorosilacyclohexane compound is reacted with a reducing agent under mild conditions not permitting the ester to be reduced, hydrosilacyclohexane compounds of the formulas (IV) and (V) wherein W is hydrogen is obtained. Examples of the reducing agent include metal hydrides such as sodium hydride, calcium hydride, trialkylsilanes, boranes, dialkyl aluminium compounds and the like, and complex hydrides such as lithium aluminium hydride, sodium borohydride, lithium borohydride, potassium borohydride, tributylammonium borohydride and the like. Although not limitative, the reduction of the halosilacyclohexane is carried out preferably at a temperature of from −50° to 100° C., more preferably from −20° to 70° C.

If the thus obtained product is in the form of steric isomers, a trans isomer is isolated and purified through known purification procedures such as recrystallization, chromatography and the like.

The starring carboxylic acid of the formula (2), (3), (5) or (6) is a novel intermediate and the preparation thereof is described.

(A) The preparation of the carboxylic acid of the following formula (A) where the substituent is a methyl group or an aryl group, i.e. W=CH$_3$ or an aryl group such as phenyl or tolyl, is described (a)

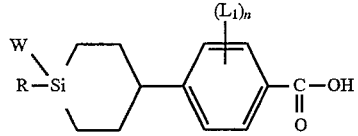
(A)

wherein W is methyl or aryl and $L_1$ and n are as defined hereinbefore.

This type of silacyclohexane compound is prepared from a silacyclohexanone compound of the following formula (a-1)

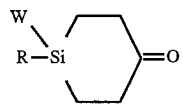
(a-1)

The silacyclohexanone of the formula (a-1) and the preparation thereof are set out in our Japanese Patent Application No. 6-78125, filed Mar. 24, 1994 (corresponding to U.S. patent application Ser. No. 408,961, filed Mar. 23, 1995) and also in Journal of Organometal Chem., Vol. 133 (1) pp. 7 to 17 (1977) and Journal of Organometal Chem. Vol. 37 (4), pp. 2323 to 2327 (1972).

The preparation of the compound of the above formula (A) comprises the steps of: coupling of the silacyclohexanone with an organometallic compound; dehydrogenation reaction and hydrogenation or hydrogenolysis; removal of a protective group; and oxidation of the resultant aldehyde, alcohol or methyl-bearing compound to obtain a compound of the formula (A).

This reaction sequence (a-2) is shown below.

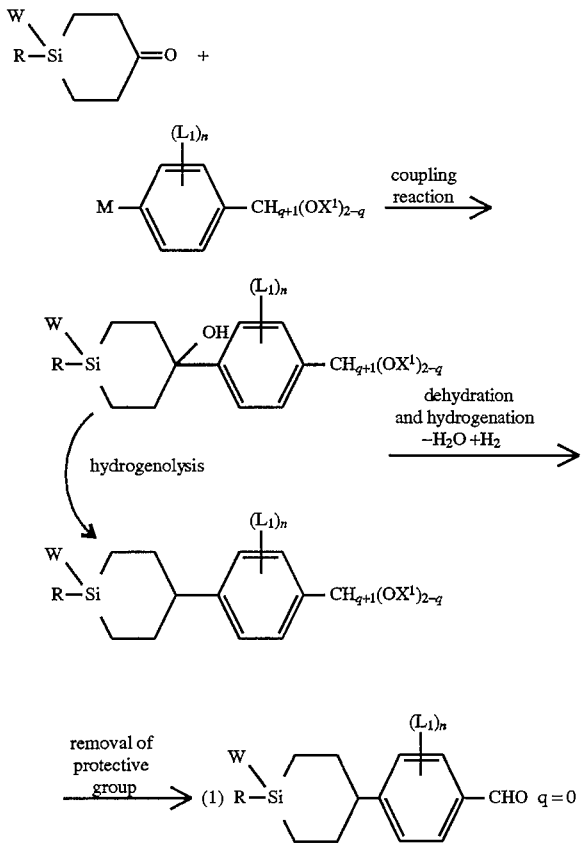

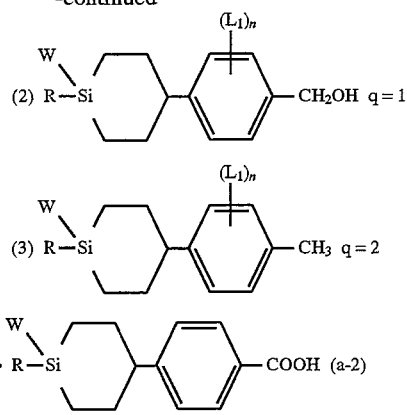

In the above reaction sequence (a-2), q is 0, 1 or 2, $X^1$ is a protective group, and M represents a metal derived from the organometallic compound. The protective group may differ depending on the value of q, e.g. the protective group may be methyl, ethyl, ethylene or propylene for q=0 and $CCH_3$- or $CH_3OSi(CH_3)2$- for q=1.

(1) In the first step, the silacyclohexanone is coupled with an organometallic reagent or compound. Examples of the organometallic reagent include Grignard reagents, organozinc reagents, organolithium reagents, organotitanium reagents and the like. Using any of the reagents, the reaction proceeds in high yield. Although depending on the type of organometallic reagent, the reaction is conducted under conditions of a temperature of −70° C. to 150° C. and a time of 30 minutes to 5 hours. More particularly, the reaction temperature ranges from −70° C. to 0° C. for organolithium reagents and from room temperature to 150° C. for the Mg, Ti and Zn-containing reagents. The coupling reaction is usually effected in solvents including ethers such as diethyl ether, tetrahydrofuran, dioxane and the like, and hydrocarbons such as benzene, toluene, xylene, mesitylene, hexane, heptane, octane and the like. These solvents may be used singly or in combination.

(2) The resultant alcohol is then subjected to hydrogenolysis to obtain a cyclohexylphenol compound. Alternatively, the alcohol may be first dehydrated with an acid catalyst and then the resultant double bond is hydrogenated to obtain the cyclohexylphenol compound. The hydrogenolysis or hydrogenation reaction is carried out at a temperature of from 0° to 150° C., preferably from 20° to 100° C. at a pressure ranging from an atmospheric pressure to 20 kg/cm².

The catalysts used for the hydrogenolysis or hydrogenation include palladium, platinum, rhodium, nickel, ruthenium and the like metals. Preferably, these metals are used in the form of combinations or as oxides such as palladium-carbon, palladium-barium sulfate, palladium-diatomaceous earth, platinum oxide, platinum-carbon, rhodium-carbon, Raney nickel, palladium oxide, nickel-diatomaceous earth and the like. More preferably, palladium or nickel catalysts are used.

The acids used for the dehydration include inorganic acids such as hydrochloric acid, sulfuric acid, nitric acid, perchloric acid and the like, and organic acids such as p-toluenesulfonic acid, camphorsulfonic acid, trifluoroacetic acid and the like. In order to quickly remove the resultant water, hydrocarbon solvents such as benzene, toluene, xylene, cumene, hexane, iso-octane and the like are used to permit the reaction to proceed more rapidly through the azeotropy.

(3) Subsequently, the protective group, $X^1$, is removed to obtain an aldehyde for q=0, an alcohol for q=1 and a methyl-bearing compound for q=2 as shown in the reaction sequence (a-2). The protective group may be removed according to any known procedure as set out, for example, by Theodora W. Greene and Peter G. M. Wuts, "Protective groups in Organic Synthesis" John Wiley & Sons. INC.

(4) Thereafter, these compounds are then oxidized by any known procedures to obtain a carboxylic acid of the afore-indicated formula (A). A typical oxidation procedure which is applicable to the oxidation of the compounds set out above is described, for example, in Oxidation and Reduction I-1 "Oxidation in Organic Chemistry" published by Maruzen.

More particularly, the aldehyde may be oxidized using permanganates such as potassium permanganate, sodium permanganate and the like, chromic acid, oxygen, hydrogen peroxide, silver (I) oxide, silver (II) oxide and the like.

Likewise, the alcohol may be oxidized using permanganates as used above, chromic acid, oxygen, nickel peroxide, perruthenate and the like. The methyl group may be oxidized with permanganates, nitric acid and the like.

(b)

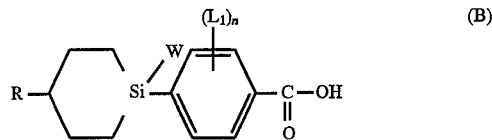

wherein W is as defined in the formula (A).

This type of acid compound is prepared from a silacyclohexanone compound of the following formula (b-1)

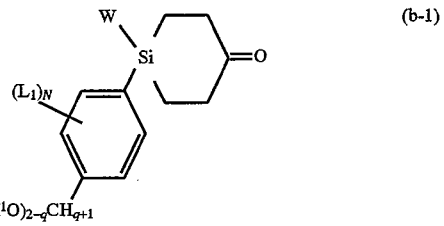

wherein $X^1$ is a protective group as used in (a) above.

This substituted silacyclohexanone compound (b-1) is prepared in a manner as set forth in (a).

The compound of the formula (B) is prepared by a process which comprises the steps of: coupling reaction with an organometallic compound; dehydration and hydrogenation or Wittig reaction and hydrogenation to obtain an alkylsilacyclohexane compound; removal of the protective group. The reaction sequence (b-2) is shown below.

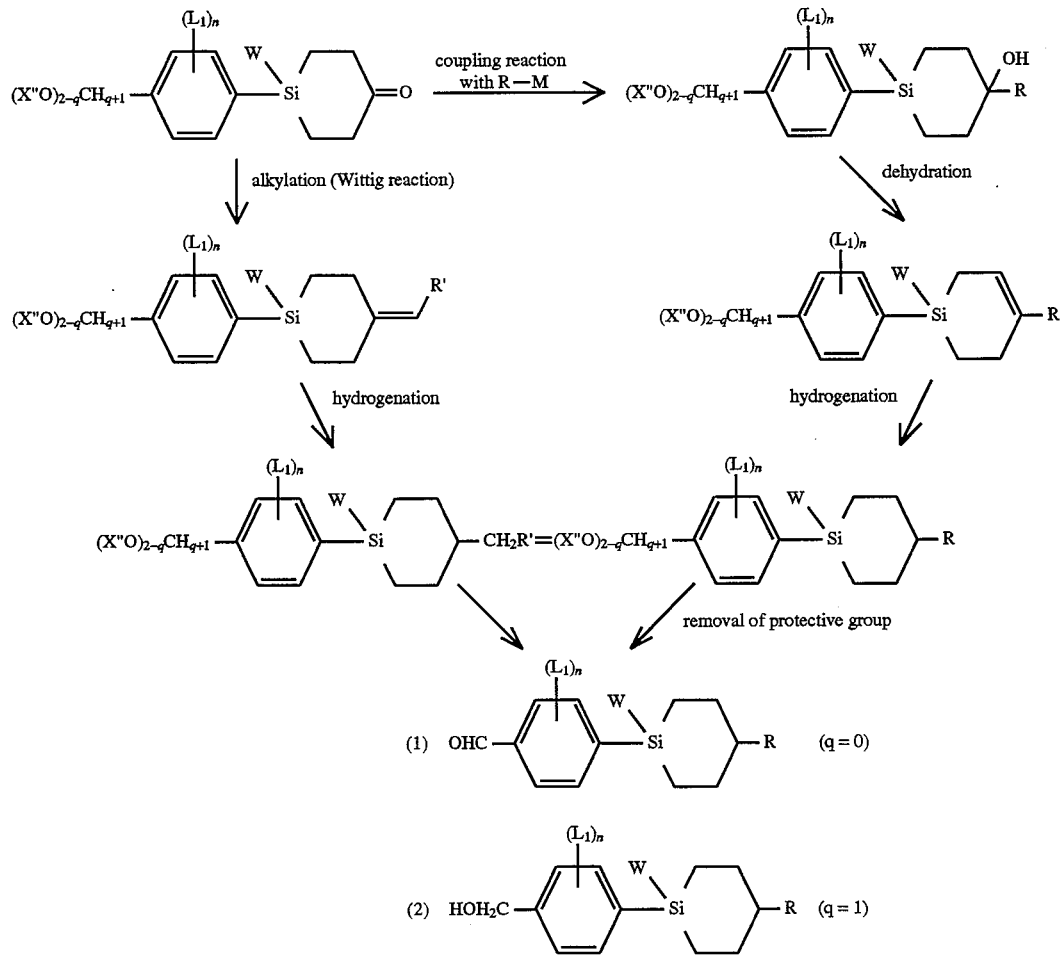

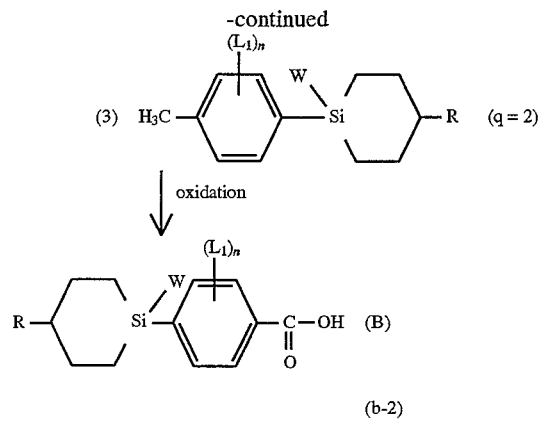

(b-2)

wherein R is a group as defined in the formula (I) and is equal to —CH$_2$R', and X$^1$ is a protective group as in (a) above. The respective steps of the above reaction sequence are as follows.

(1) The silacyclohexanone is converted to an alkylsilacyclohexane compound through two ways. One way includes coupling reaction with an organometallic compound, R-M, followed by dehydration and hydrogenation. The other way includes the alkylation reaction and hydrogenation. The dehydration and hydrogenation reaction conditions and reagents used are those as in (a)

The coupling reaction with an organometallic compound, R-M, is carried out in the same manner as in (1) of (a). More particularly, the silacyclohexanone is coupled with an organometallic compound such as Grignard reagents, organotitanium reagents and the like. Although depending on the type of organometallic reagent, the reaction is conducted under conditions of a temperature of –70° to 150° C. and a time of 30 minutes to 5 hours. More particularly, the reaction temperature ranges from –70°° C. to 0° C. for organolithium reagents and from room temperature to 150° C. for Grignard reagents. The coupling reaction is usually carried out in solvents including ethers such a diethyl ether, tetrahydrofuran, dioxane and the like, and hydrocarbons such as benzene, toluene, xylene, mesitylene, hexane, heptane, octane and the like. These solvents may be used singly or in combination.

The alkylation reaction of the silacyclohexnone compound is effected through the Wittig reaction with a ylide compound obtained from an alkyltriphenylphosphonium salt by the action of a base. The alkyltriphenylphosphonium salts used in the reaction include, for example, methyltriphenylphosphonium chloride, methyltriphenylphosphonium bromide, methyltriphenylphosphonium iodide, ethyltriphenylphosphonium chloride, ethyltriphenylphosphonium bromide, ethyltriphenylphosphonium iodide and the like. The bases used for the formation of the ylide compound include organolithium compounds such as n-butyl lithium, s-butyl lithium, t-butyl lithium, methyl lithium, phenyl lithium and the like, alkoxides such as sodium methoxide, sodium ethoxide, potassium t-butoxide, and the like, dimsyl sodium, and the like. The Wittig reaction is performed in ethers such as tetrahydrofuran, diethyl ether, di-n-butyl ether, 1,4-dioxane and the like which may be used singly or in combination with hydrocarbons such as n-hexane, n-heptane, iso-octane, benzene, toluene, xylene, cumene and the like and aprotic polar solvents such as N,N-dimethylformamide, dimethylsulfoxide, hexamethylphosphoric triamide and the like. Preferred reaction conditions include a temperature of from 0° C. to a refluxing temperature of the solvent used.

(2) Then, the protective group, X', is removed from the compound obtained above in the same manner as in (a), thereby obtaining three types of compounds (1) to (3) mentioned in the reaction sequence (b-2).

(3) The oxidation to these compounds may be performed by known procedures as in (a).

On the other hand, the silacyclohexane compounds of the following formulas (VI) and (VII) may be likewise prepared using from a carboxylic acid and a phenol

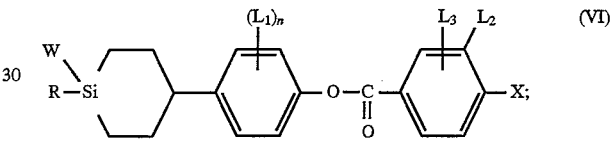

and

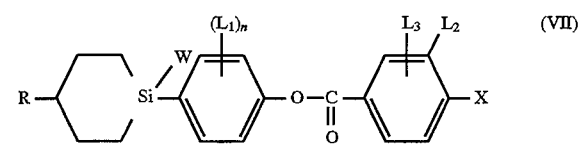

More particularly, when a carboxylic acid of the following general formula (8)

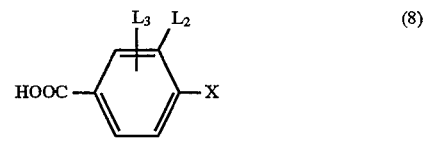

wherein X, L$_2$ and L$_3$ have, respectively, the same meanings as defined hereinbefore, is reacted with a phenol of the following general formula (9) or (10)

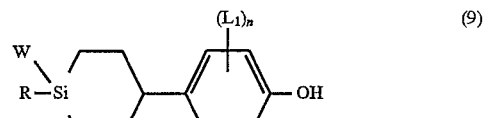

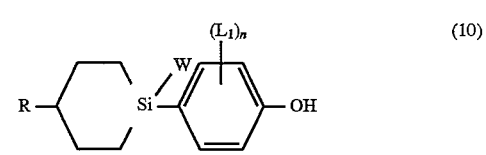

the silacyclohexane compounds of the formulas (VI) to (VII) are prepared. Similar esterification reaction conditions and reagents as used in the methods (1) and (2) for the compounds of the formulas (IV) and (V) may be likewise used.

The phenol compound of the formula (9) or (10) is a novel intermediate compound and the preparation thereof is described. Like the 4-(4-silacyclohexyl) cyclohexylcarboxylic acids having set out hereinbefore, the preparation of the phenol of the formula (9) or (10) differs depending on the type thereof.

(A') The preparation of the phenols where the substituent is methyl or aryl, is described for different types (a') and (b') of silicon-containing phenols.

phenol of the formula (9) is prepared substantially in the same manner as the corresponding acid of the formula (A) using a different type of starring organometallic compound. More particularly, the silacyclohexanone is subjected to coupling reaction with an organometallic compound of the type depicted in the formula (a'-1), dehydration and hydrogenation or hydrogenolysis and removal of the protective group. These steps are carried out substantially in the same manner as described with respect to the carboxylic acid (A).

(a')

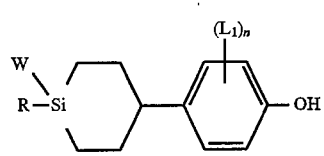

(9)

(b')

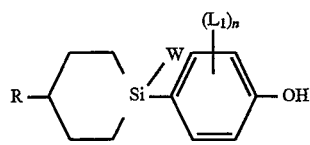

(10)

This compound is prepared according to the following reaction sequence (a'-1)

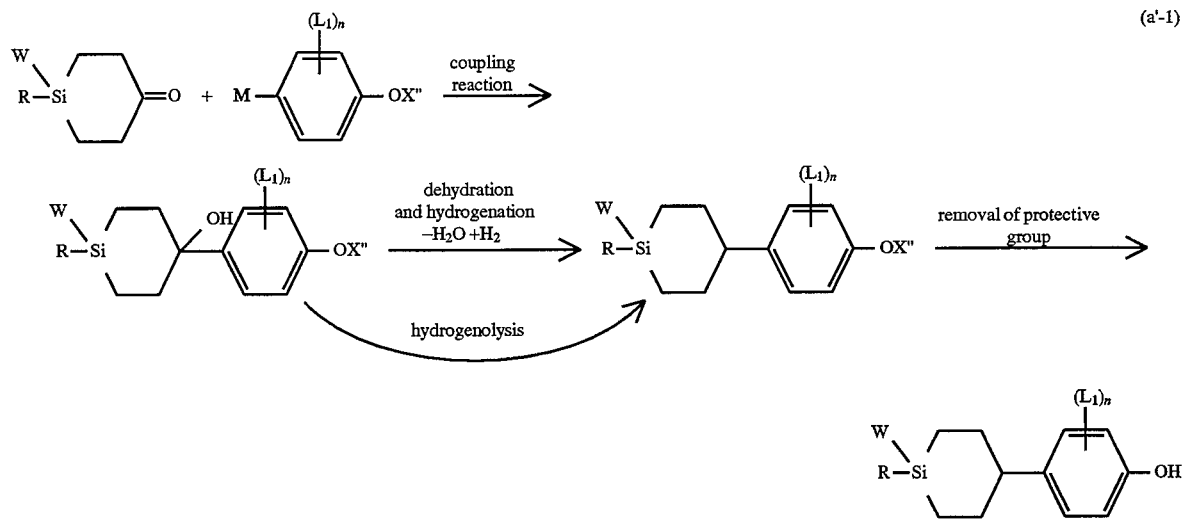

(a'-1)

In the above sequence, X" is a protective group such as a t-butyldimethylsilyl group, an alkoxymethyl group such as a methoxymethyl group, a benzyl group or the like. The phenol of the formula (9) is prepared substantially in the This type of phenol may be prepared according to different three procedures, two of which are shown below as a reaction sequence (b'-1)

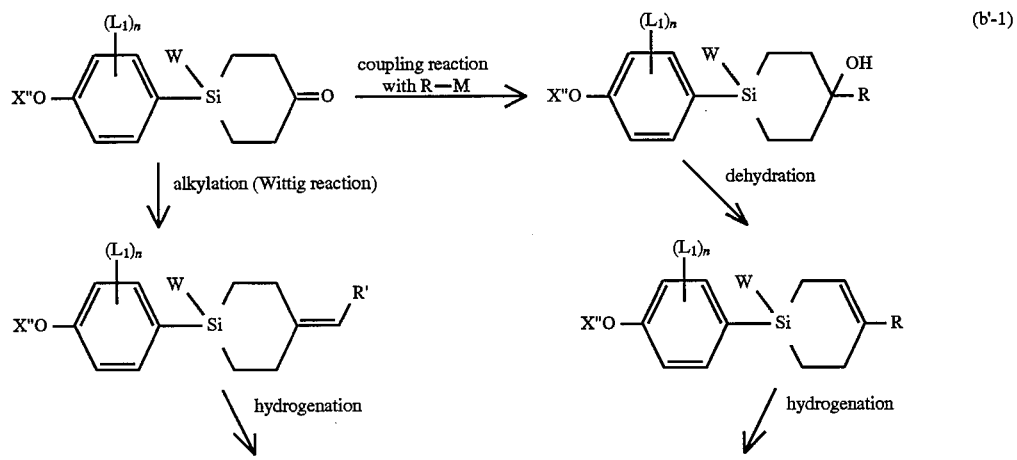

(b'-1)

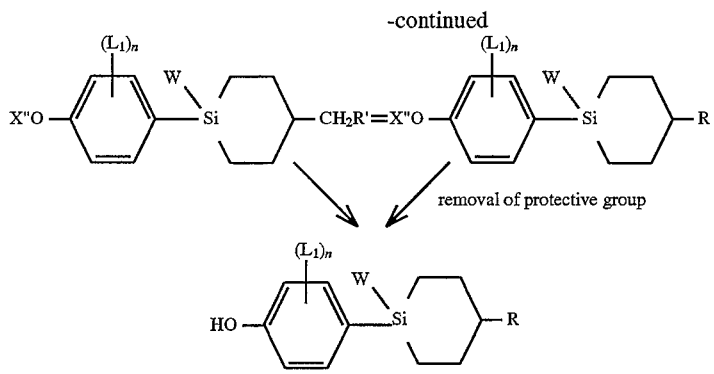

In one of the above two processes, the silacyclohexanone is reacted with an organometallic compound such as a Grignard reagent or an organolithium compound, dehydrated and hydrogenated, followed by removal of the protective group to obtain an intended phenol. Alternatively, the silacyclohexanone is alkylated through the Wittig reaction and hydrogenated, followed by removal of the protective group to obtain an intended phenol. In the above reaction sequence, W is methyl or aryl, $L_1$, n, R, and X" are as defined hereinbefore.

Still alternatively, the phenol of the formula (10) may be obtained according to the following procedure using a silacyclohexanone having two aryl groups joined to the silicon atom at the 4 position.

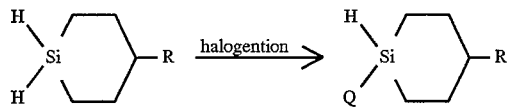

wherein X is Cl or Br. The halogenation may be carried out, for example, by the following procedures (1) to (3).

(1) The starring silacyclohexane compound is mixed with a solvent such as an alkyl halide, e.g. $CH_2Cl_2$, $CHCl_3$, $CCl_4$ or the like, into which a halogenaring agent such as $Cl_2$ or $Br_2$ is dropped, followed by reaction under conditions of a temperature of from 0° to 50° C. and a time of 5 minutes to 3 hours. The secondarily produced hydrogen halide and the solvent are removed under reduced pressure to obtain an intended monohalogenated compound.

(2) The starring compound is mixed with a solvent such as an ether, e.g. diethyl ether, tetrahydrofuran or the like, and $CuCl_2$ and CuI, followed by agitation under conditions of a temperature of from 0° to 50° C. and a time of from 1 to 50 hours. After completion of the reaction, the $CuCl_2$ and CuI used as the halogenaring agent are removed by filtration, followed by further removal of the solvent under reduced pressure to obtain an intended monohalogenated compound.

(3) The starring compound is dropped in a mixture of a halogenaring agent such as $Cl_4$ and a halogenaring initiator or a radial generator such as benzoyl peroxide in an alkyl halide solvent as used in (1) above. The resultant mixture is

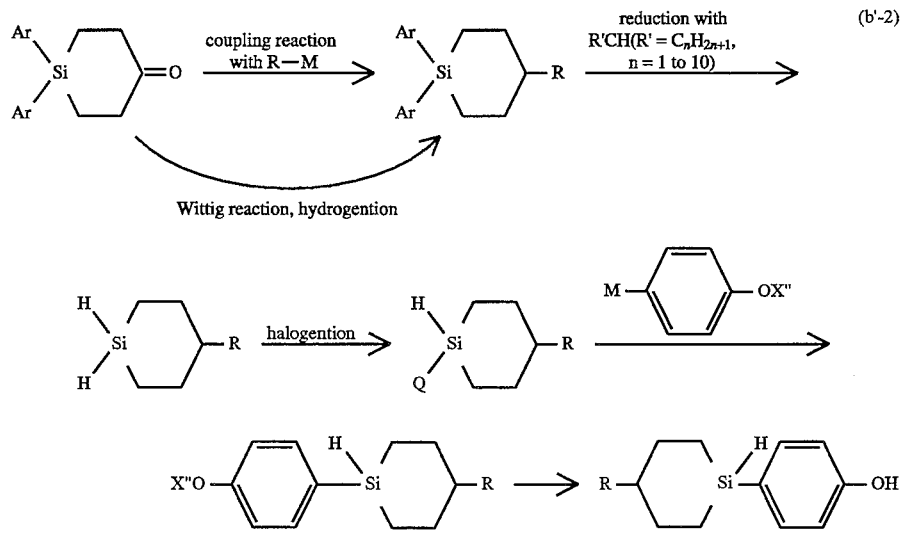

In the above reaction sequence, the starring silacyclohexanone is coupled with an organometallic compound, dehydrated and hydrogenated or is subjected to the Wittig reaction and hydrogenated to obtain a corresponding silacyclohexane compound in the same manner as in (b'-1). The thus obtained compound is reduced using a compound of R'CH such as $CH_2=CH_2$, followed by halogenation by a usual manner. More particularly, the silacyclohexane compound is halogenated in the following manner reacted under conditions of a temperature of from 0° to 50° C. and a time of 30 minutes to 10 hours. After completion of the reaction, the solvent is removed by distillation under reduced pressure to obtain an intended halogenated compound.

Then, an organometallic compound is reacted with the halogenated silacyclohexane, followed by removal of the protective group of X" to obtain an intended phenol. The series of the reactions are known per se and are not described herein in detail.

The silacyclohexane compounds of the invention are appropriately used in combination with known liquid crystal compounds to provide a liquid crystal composition. Such known liquid crystal compounds suitable for this purpose include those compounds of the general formulas (13) and (14)

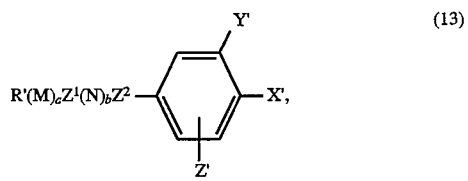

and

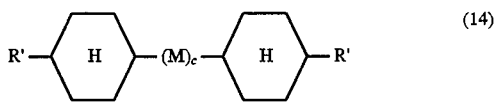

In the above formula (13) and (14), each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms and is same as defined as R in the afore-indicated formula (I); X' is same as X defined hereinbefore and represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents H, F or Cl , or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted trans-1,4-cyclohexylene group which has, if substituted, one or more substituents such as F, Cl , Br, CN and an alkyl group having from 1 to 3 carbon atoms, (2) a trans-1,4-cyclohexylene group wherein one $CH_2$ unit or two $CH_2$ units, not adjacent to each other, of the cyclohexane ring are replaced by O or S, (3) a 1,4-cyclohexenylene group, (4) an unsubstituted or substituted 1,4-phenylene group having, if substituted, one or two F, Cl, $CH_3$ and/or CN groups and (5) a 1,4-phenylene group in which one or two CH units of the phenylene group are replaced by nitrogen atom, a and b are, respectively, 0, 1 or 2 provided that a+b=1, 2 or 3, and c is 0, 1 or 2; and $Z^1$ and $Z^2$ are, respectively, —$CH_2CH_2$—, —CH=CH—, —C≡C—, —$CO_2$—, —OCO—, —$CH_2O$—, —$OCH_2$— or single bond.

In the above formulas (13) and (14), if both and c is 2, M's may be the same or different and are independently selected from the groups (1) to (5) set forth above. If h is 2, N's may be the same or different and are independently selected from the groups (1) to (5) set forth above.

The silacyclohexane compounds which may be used singly or in combination should preferably be present in a liquid crystal phase or composition in an amount of from 1 to 50 mole %, preferably from 5 to 30 mole %. As a matter of course, the liquid crystal composition may further comprise polychromatic dyes capable of forming colored guest-host systems, additives capable of imparring dielectric anisotropy, viscosity modifiers, and/or additives for changing the direction of alignment of a nematic phase.

In practice, the liquid crystal phase or composition comprising at least one compound of the invention is suitable for use in liquid crystal display devices wherein the composition is hermetically sealed between transparent substrates each having an electrode of a desired shape. If necessary, the device may have various types of undercoarings, overcoarings for controlling the alignment, polarizers, filters and reflective layers as is known in the art. Alternatively, a multi-layer cell may be used to incorporate the compounds of the invention. The liquid crystal display device may be used in combination with other types of display devices, semiconductor substrates, and light sources.

With the compounds of the invention whose value of Δε is positive or is close to zero, the liquid crystal display device is driven according to a twisted nematic (TN) system, a super twisted nematic (STN) system or a guest-host (GH) system. For the compounds whose value of Δε is negative, a dynamics scattering mode (DSM) system, an electrically controlled birefringence(ECB) system, a guest-host (GH) system and the like known in the art may be adopted.

The invention is more particularly described by way of examples.

EXAMPLE 1

Preparation of 4-cyanophenyl trans-4-(4-methyl-4-n-pentyl-4-silacyclohexyl)benzoate 12.0 g of N,N-dicyclohexylcarbodiimide (DCC) was added to a mixture of 15.3 g of trans-4-(4-methyl-4-n-pentyl-4-silacyclohexyl)benzoic acid, 6.50 g of 4-cyanophenol, 7.00 g of 4-dimethylaminopyridine and 180 ml of methylene chloride at room temperature. The resultant reaction mixture was agitated for 8 hours at room temperature, after which the resultant N,N'-dicyclohexyl urea was removed by filtration. The filtrate was washed with brine, dried and concentrated, followed by silica gel chroromatography to obtain 9.98 g (yield: 49%) of the intended product.

EXAMPLE 2

Preparation of 4-trifluoromethoxyphenyl trans-4-(4-methyl-4-n-propyl-4-silacyclohexyl )benzoate The general procedure of Example 1 was repeated using trans 4(4-methyl-4-n-propyl-4-silacyclohexyl) benzoic acid and 4trifluoromethyoxyphenol, thereby obtaining the intended product.

EXAMPLE 3

Preparation of 4-trifluoromethoxyphenyl trans-4-(4-n-propyl-4silacyclohexyl)benzoate A mixture of 15.8 g of 4-(4-phenyl-4-n-propyl-4-silacyclohexyl)benzoic acid, 15.0 g of triphenylphosphine and 80 ml of carbon tetrachloride was agitated for 12 hours under reflux. A mixture of 9.0 g of 4-trifluoromethoxyphenol and 20 ml of pyridine was added to the first-mentioned mixture, followed by further addition of 80 mg of 4-dimethylaminopyridine and agitation for 10 hours at room temperature. The resultant mixture was poured into dilute hydrochloric acid and extracted with ethyl acetate. The resultant ethyl acetate solution was washed with brine, dried and concentrated, followed by purification through silica gel chromatography to obtain 17.9 g (yield: 77%) of 4-trifluoromethoxyphenyl) 4-(4-phenyl-4-n-propyl-4-silacyclohexyl)benzoate. The results of IR and NMR analyses are shown below.

IR (KBr, disc) $v_{max}$: 2918, 2868, 1741, 1606, 1504, 1259, 1223, 1176, 1062, 879 cm$_{-1}$ $^1$H-NMR (CDCl$_3$) δ:0.7–2.7 (16H, m), 7.1–8.3 (13H, m)

35 ml of a carbon tetrachloride solution of 1.0 mole of iodine monochloride was added to a mixture of 17.2 g of the thus obtained product and 200 ml of carbon tetrachloride at 0° C. and agitated for 12 hours. The reaction mixture was concentrated under reduced pressure to obtain 15.0 g (yield: 95%) of (4-trifluoromethoxyphenyl) 4-(4-chloro-4-n-propyl-4-silacyclohexyl)benzoate. The results of gas chromatography-mass spectroscopy (GC-MS) are shown below.

GC-MS (m/z)$^+$: 456, 413, 279

10.8 g of the thus obtained product was added to 300 ml of a tetrahydrofuran solution of 0.05 moles of lithium aluminium hydride and agitated at −10° C. for 15 minutes. The reaction mixture was poured into dilute hydrochloric acid and extracted with methylene chloride. The methylene chloride solution was washed with brine, dried and concentrated, followed by purification through silica gel chromatography to obtain 4.45 g (yield: 45%) of the intended product. The results of IR analysis and measurement of phase transition temperatures are shown below.

IR (KBr, disc) $v_{max}$: 2914, 2873, 2114, 1740, 1506, 1273, 1263, 1230, 1221, 1186, 1161, 1076, 987, 877, 835 cm$^{-1}$
$T_{CN}$ (crystal-nematic phase transition temperature)=100° C.
$T_{NI}$ (nematic phase -isotropic phase transition temperature) =124° C.

EXAMPLE 4

Preparation of 4-cyanophenyl trans-4-(4-n-pentyl-4-silacyclohexyl)benzoate

The general procedure of Example 3 was repeated using 4-fluorophenol and 4-(4-phenyl-4-n-pentyl-4-silacyclohexyl)benzoic acid, thereby obtaining the intended product.

EXAMPLE 5

Preparation of 4-fluorophenyl trans-4-(4-n-pentyl-4-silacyclohexyl)benzoate

The general procedure of Example 3 was repeated using 4-cyanophenol and 4-(4-phenyl-4-n-pentyl-4-silacyclohexyl)benzoic acid, thereby obtaining the intended product.

EXAMPLE 6

Preparation of 4-chlorophenyl trans-4-(4-n-propyl-4-silacyclohexyl)benzoate

The general procedure of Example 3 was repeated using 4chlorophenol, thereby obtaining the intended product.

EXAMPLE 7

Preparation of 4-n-propylphenyl trans-4-(4-n-propyl-4-silacyclohexyl)benzoate

The general procedure of Example 3 was repeated using 4-n-propylphenol, thereby obtaining the intended product.

EXAMPLE 8

Preparation of 4-n-pentylphenyl trans-4-(4-n-propyl-4-silacyclohexyl)benzoate

The general procedure of Example 3 was repeated using 4-n-pentylphenol, thereby obtaining the intended product. The results of IR analysis and measurement of phase transition temperatures are shown below.

IR (KBr, disc) $v_{max}$: 2924, 2854, 2100, 1736, 1512, 1263, 1213, 1184, 1070, 985, 885, 839 cm$^{-1}$
$T_{CN}$ (crystal phase-nematic phase transition temperature)= 75° C.
$T_{NI}$ (nematic phase-isotropic phase transition temperature) =147° C.

EXAMPLE 9

Preparation of (3,4-difluorophenyl) trans-4-(4-n-propyl-4-silacyclohexyl)benzoate The general procedure of Example 3 was repeated using 3,4-difluorophenol, thereby obtaining the intended product. The results of IR analysis and measurement of phase transition temperatures are shown below.

IR (KBr, disc) $v_{max}$: 2906, 2848, 2123, 1736, 1516, 1245, 1205, 1144, 1063, 985, 876, 837 cm$^{-1}$
$T_{CN}$ (crystal phase-nematic phase transition temperature)= 85° C.
$T_{NI}$ (nematic phase-isotropic phase transition temperature) =89° C.

EXAMPLE 10

Preparation of (4-cyano-3-fluorophenyl) trans-4-(4-n-propyl-4-silacyclohexyl)benzoate The general procedure of Example 3 was repeated using 3-cyano-4-fluorophenol, thereby obtaining the intended product.

EXAMPLE 11

Preparation of (3,5-difluoro-4-difluoromethoxyphenyl) trans-4-(4-n-propyl-4-silacyclohexyl)benzoate The general procedure of Example 3 was repeated using 3,5-difluoro-4-difluoromethoxyphenol, thereby obtaining the intended product.

EXAMPLE 12

Preparation of (4-methoxyphenyl) trans-4-(4-n-propyl4-silacyclohexyl)benzoate

The general procedure of Example 3 was repeated using 4-methoxyphenol, thereby obtaining the intended product.

EXAMPLE 13

Preparation of (4-chloro-3-fluorophenyl) trans-4-(4-n-pentyl-4-silacyclohexyl)benzoate The general procedure of Example 3 was repeated using 4-chloro-3-fluorophenol and 4-(4-phenyl-4-n-pentyl-4- silacyclohexyl)benzoic acid, thereby obtaining the intended product.

EXAMPLE 14

Preparation of (3,4,5-trifluorophenyl) trans-4-(4-n-pentyl-4-silacyclohexyl)benzoate The general procedure of Example 3 was repeated using 3,4,5-trifluorophenol and 4-(4-phenyl-4-n-pentyl-4-silacyclohexyl)benzoic acid, thereby obtaining the intended product.

EXAMPLE 15

Preparation of (3,4-dichlorophenyl) trans-4-(4-(5-methoxypentyl)-4-silacyclohexyl)benzoate The general procedure of Example 3 was repeated using 3,4-dichlorophenol and 4-(4-phenyl-4-(5-methoxypentyl)-4-silacyclohexyl)benzoic acid, thereby obtaining the intended product.

EXAMPLE 16

Preparation of (4-chlorophenyl) trans-4-(4-(4-pentenyl)-4-silacyclohexyl)benzoate The general procedure of Example 3 was repeated using 4-chlorophenol and 4-(4-phenyl-4-(4-pentenyl)-4-silacyclohexyl)benzoic acid, thereby obtaining the intended product.

EXAMPLE 17

Preparation of (trifluoromethylphenyl) trans-4-(4-(3-methylbutyl)-4-silacyclohexyl)benzoate The general procedure of Example 3 was repeated using trifluoromethylphenol and 4-(4-phenyl-4-(3methylbutyl)-4-silacyclohexyl)benzoic acid, thereby obtaining the intended product.

EXAMPLE 18

Preparation of (4-trifluoromethoxyphenyl) trans-4-(4-(4-fluorobutyl)-4-silacyclohexyl)benzoate The general procedure of Example 3 was repeated using 4-trifluorophenol and 4-(4-phenyl-4-(4-fluorobutyl)-4-silacyclohexyl)benzoic acid, thereby obtaining the intended product.

EXAMPLE 19

Preparation of (3,4-difluorophenyl) trans-4-(4-(4-fluoropentyl)-4-silacyclohexyl)benzoate The general procedure of Example 3 was repeated using 3,4-difluorophenol and 4-(4-phenyl-4-(4-fluoropentyl)-4-silacyclohexyl)benzoic acid, thereby obtaining the intended product.

EXAMPLE 20

Preparation of (4-fluorophenyl) trans-2,6-difluoro-4-(4-n-pentyl-4-silacyclohexyl)benzoate The general procedure of Example 3 was repeated using 4-fluorophenol and trans-2,6-difluoro-4-(4-phenyl-4-n-pentyl-4-silacyclohexyl)benzoic acid, thereby obtaining the intended product.

EXAMPLE 21

Preparation of (4-chlorophenyl) trans-4-(4-n-propyl-4-silacyclohexyl)benzoate

The general procedure of Example 3 was repeated using 4-chlorophenol, thereby obtaining the intended product.

EXAMPLE 22

Preparation of (4ochlorophenyl) trans-4-(4-n-propyl-1-fluoro-1-silacyclohexyl)benzoate The general procedure of Example 3 was repeated using 4-chlorophenol and 4-(4-phenyl-4-n-propyl-1-fluoro-1-silacyclohexyl)benzoic acid, thereby obtaining the intended product.

EXAMPLE 23

A liquid crystal mixture was prepared by mixing 20% by mole of trans-4-(2-(3,4-difluorophenyl)ethyl)-1-pentylcyclohexane, 32% by mole of 4-(trans-4-(trans-4-ethylcyclohexyl)cyclohexyl)-1,2-difluorobenzene, 28% by mole of 4-(trans-4-(trans-4-n-propylcyclohexyl)cyclohexyl)-1,2-difluorobenzene, and 20% by mole of 4-(trans-4-(trans-4-n-pentylcyclohexyl)cyclohexyl)-1,2-difluorobenzene. The mixture had the following phase transition temperature.

$T_{NI}$ (nematic phase-isotropic phase transition temperature) =75° C.

Viscosity (20° C.)=19 cps.

85% by mole of the above mixture was further mixed with 15% by mole of (4-n-pentylphenyl) trans-4-(4-n-propyl-4-silacyclohexyl)benzoate. The resultant mixture exhibited a nematic-isotropic phase transition temperature shifted to a higher temperature side without any substantial rise of viscosity as shown below.

$T_{NI}$ (nematic phase-isotropic phase transition temperature) =86° C.

Viscosity (20° C.)=21 cps.

EXAMPLE 24

Preparation of(4-(4-methyl-4-n-pentyl-4-silacyclohexyl)phenyl) trans-4-cyanobenzoate 2.50 g of N,N'-dicyclohexylcarbodiimide (DCC) was added to a mixture of 1.90 g of 4-cyanobenzoic acid, 2.76 g of 4-(4-methyl-4-n-pentyl-4-silacyclohexyl)phenol, 1.50 g of 4-dimethylaminopyridine and 30 ml of methylene chloride at room temperature. The resultant reaction mixture was agitated for 8 hours at room temperature, after which the resultant N,N'-dicyclohexyl urea was removed by filtration. The filtrate was washed with brine, dried and concentrated to obtain a residue, followed by silica gel chromatography to obtain 2.35 g (yield: 58%) of the intended product.

EXAMPLE 25

Preparation of (4-(4-methyl-4-n-propyl-4-silacyclohexyl)phenyl) trans-4-trifluoromethoxybenzoate The general procedure of Example 24 was repeated using trans -4-trifluoromethoxybenzoic acid and 4-(4-methyl-4-n-propyl-4-silacyclohexyl)phenol, thereby obtaining the intended product.

EXAMPLE 26

Preparation of (4-(4-n-propyl-4-silacyclohexyl) phenyl) trans-4-trifluoromethoxybenzoate 30.9 g of 4-trifluoromethoxybenzoyl chloride was dropped in a mixture of 31.1 g of 4-(4-phenyl-4-n-propyl-4-silacyclohexyl)phenol, 150 ml of pyridine and 100 mg of 4-dimethylaminopyridine at 0° C., followed by agitation at room temperature for 10 hours. Thereafter, the reaction mixture was charged into dilute hydrochloric acid and extracted with ethyl acetate. The ethyl acetate solution was washed with brine, dried and concentrated, followed by purification of the resultant residue through silica gel chromatography to obtain 33.9 g (yield: 68%) of 4-(4-(phenyl-4-n-propyl-4-silacyclohexyl) phenyl) 4-trifluoromethoxybenzoate. The results of IR and NMR analyses are shown below.

IR (KBr, disc) $v_{max}$: 2924, 2868, 1738, 1605, 1508, 1267, 1213, 1167, 1078, 978, 879 cm$^{-1}$ $^1$H-NMR (CDCl$_3$) δ: 0.7–2.7 (16H, m), 7.0–7.7 (9H, m), 8.1–8.3 (4H, m) ppm 25 ml of a carbon tetrachloride solution of 1.0 mole of iodine monochloride was added to a mixture of 10.0 g of the thus obtained product and 150 ml of carbon tetrachloride at room temperature and agitated for 1 hour. The reaction mixture was concentrated under reduced pressure to obtain crude 4-(4-chloro-n-propyl-4-silacyclohexyl)phenyl 4-fluoromethoxybenzoate.

The thus obtained product was added to a mixture of 400 mg of lithium aluminium hydride and 50 ml of diethyl ether at –40° C., followed by agitation at –40° C. for 25 minutes. The reaction mixture was poured into dilute sulfuric acid and extracted with methylene chloride. The methylene chloride solution was washed with brine, dried and concentrated, followed by purification through silica gel chromatography to obtain 3.56 g (yield: 42%) of the intended product. The results of IR analysis and measurement of phase transition temperatures are shown below.

IR (KBr, disc) $v_{max}$: 2920, 2872, 2108, 1741, 1606, 1508, 1259, 1198, 1165, 1076, 985, 879 cm$^{-1}$ $T_{CS}$ (crystal phase-smectic phase transition temperature)= 84.8° C.

$T_{SN}$ (smectic phase-nematic phase transition temperature)= 141.0° C.

$T_{NI}$ (nematic phase-isotropic phase transition temperature) =154.6° C.

EXAMPLE 27

Preparation of (4-(4-n-propyl-4-silacyclohexyl) phenyl) trans-4-cyanobenzoate

The general procedure of Example 26 was repeated using 4-cyanobenzoyl chloride, thereby obtaining the intended product.

EXAMPLE 28

Preparation of (4-(4-n-propyl-4-silacyclohexyl) phenyl) trans-4-fluorobenzoate

The general procedure of Example 26 was repeated using 4-fluorobenzoyl chloride, thereby obtaining the intended product.

EXAMPLE 29

Preparation of (4-(4-n-propyl-4-silacyclohexyl) phenyl) trans-4-chlorobenzoate

The general procedure of Example 26 was repeated using 4-chlorobenzoyl chloride, thereby obtaining the intended product.

EXAMPLE 30

Preparation of (4-(4-n-propyl-4-silacyclohexyl) phenyl) trans-4-n-propylbenzoate The general procedure of Example 26 was repeated using 4-n-propylbenzoyl chloride, thereby obtaining the intended product.

EXAMPLE 31

Preparation of (4-(4-n-propyl-4-silacyclohexyl) phenyl) trans-4-n-pentylbenzoate The general procedure of Example 26 was repeated using 4-n-pentylbenzoyl chloride, thereby obtaining the intended product. The results of IR analysis and measurement of phase transition temperatures are shown below.

IR (KBr, disc) $v_{max}$: 2920, 2868, 2098, 1728, 1610, 1504, 1277, 984, 889 cm$^{-1}$ $T_{CN}$ (crystal phase-nematic phase transition temperature)= 80.6° C.

$T_{NI}$ (nematic phase-isotropic phase transition temperature) =147.4° C.

EXAMPLE 32

Preparation of (4-(4-n-propyl-4-silacyclohexyl) phenyl) trans-3,4-difluorobenzoate The general procedure of Example 26 was repeated using 3,4-difluorobenzoyl chloride, thereby obtaining the intended product. The results of IR analysis and measurement of phase transition temperatures are shown below.

IR (KBr, disc) $v_{max}$: 2922, 2852, 2102, 1736, 1618, 1514, 1431, 1290, 1201, 985, 883 cm$^{-1}$ $T_{CN}$ (crystal phase-nematic phase transition temperature)= 72.8° C.

$T_{SN}$ (smectic phase-nematic phase transition temperature)= 60.1° C.

$T_{NI}$ (nematic phase-isotropic phase transition temperature) =111.0° C.

EXAMPLE 33

Preparation of (4-(4-n-pentyl-4-silacyclohexyl) phenyl) trans-4-cyano-3-fluorobenzoate The general procedure of Example 26 was repeated using 4-cyano-3-fluorobenzoyl chloride and 4-(4-phenyl-4-n-pentyl-4-silacyclohexyl)phenol, thereby obtaining the intended product.

EXAMPLE 34

Preparation of (4-(4-n-pentyl-4-silacyclohexyl) phenyl) trans-3,5-difluoro-4-difluoromethoxybenzoate The general procedure of Example 26 was repeated using trans-3,5-difluoro-4-difluorobenzoyl chloride and 4-(4-phenyl-4-n-pentyl-4-silacyclohexyl)phenol, thereby obtaining the intended product.

EXAMPLE 35

Preparation of (4-(4-n-pentyl-4-silacyclohexyl) phenyl) trans4-methoxybenzoate

The general procedure of Example 26 was repeated using 4-methoxybenzoyl chloride and 4-(4-phenyl-4-n-pentyl-4-silacyclohexyl)phenol, thereby obtaining the intended product.

EXAMPLE 36

Preparation of (4-(4-n-pentyl-4-silacyclohexyl) phenyl) trans-4-chloro-3-fluorobenzoate The general procedure of Example 26 was repeated using 4-chloro-3-fluorobenzoyl chloride and 4-(4-phenyl-4-n-pentyl-4-silacyclohexyl)phenol, thereby obtaining the intended product.

EXAMPLE 37

Preparation of (4-(4-n-pentyl-4-silacyclohexyl) phenyl) trans-3,4,5-trifluorobenzoate The general procedure of Example 26 was repeated using 3,4,5-trifluorobenzoyl chloride and 4-(4-phenyl-4-n-pentyl-4-silacyclohexyl)phenol, thereby obtaining the intended product.

EXAMPLE 38

Preparation of (4-(4-(5-methoxypentyl)-4-silacyclohexyl)phenyl) trans-3,4-dichlorobenzoate The general procedure of Example 26 was repeated using 3,4-dichlorobenzoyl chloride and 4-(4-phenyl-4-(5-methoxylpentyl)-4-silacyclohexyl)phenol, thereby obtaining the intended product.

EXAMPLE 39

Preparation of (4-(4-(4-pentenyl)-4-silacyclohexyl) phenyl) trans-4-chlorobenzoate The general procedure of Example 26 was repeated using 4-chlorobenzoyl chloride and 4-(4-phenyl-4-(4-pentenyl)-4-silacyclohexyl)phenol, thereby obtaining the intended product.

EXAMPLE 40

Preparation of (4-(4-(3-methylbutyl)-4-silacyclohexyl)phenyl) trans-4-trifluoromethylbenzoate The general procedure of Example 26 was repeated using 4-trifluoromethylbenzoyl chloride and 4-(4-phenyl-4-(3-methylbutyl)-4-silacyclohexyl)phenol, thereby obtaining the intended product.

EXAMPLE 41

Preparation of (4-(4-n-pentyl-4-silacyclohexyl)-2,6-difluorophenyl) trans-4-fluorobenzoate The general procedure of Example 26 was repeated using 4-fluorobenzoyl chloride and 4-(4-phenyl-4-n-pentyl-4-silacyclohexyl)-2,6-difluorophenol, thereby obtaining the intended product.

EXAMPLE 42

Preparation of (4-(4-n-propyl-1-silacyclohexyl) phenyl) trans-4chlorobenzoate

The general procedure of Example 26 was repeated using 4-chlorobenzoyl chloride and 4-(4-phenyl-4-n-propyl-1-silacyclohexyl)phenol, thereby obtaining the intended product.

EXAMPLE 43

Preparation of (4-(4-n-pentyl-1-silacyclohexyl) phenyl) trans-4-chlorobenzoate

The general procedure of Example 26 was repeated using 4-chlorobenzoyl chloride and 4-(4-phenyl-4-n-pentyl-1-silacyclohexyl)phenol, thereby obtaining the intended product.

EXAMPLE 44

Preparation of (4-(4-(4-fluorobutyl)-4-silacyclohexyl)phenyl) trans-4-trifluoromethoxybenzoate The general procedure of Example 26 was repeated using 4-trifluoromethoxybenzoyl chloride and 4-(4-phenyl-(4-fluorobutyl)-4-silacyclohexyl)phenol, thereby obtaining the intended product.

EXAMPLE 45

A liquid crystal mixture was prepared by mixing 20% by mole of trans-4-(2-(3,4-difluorophenyl)ethyl)-1-butylcyclohexane, 32% by mole of 4-(trans-4-(trans-4-ethylcyclohexyl) cyclohexyl)cyclohexyl)cyclohexyl)-1,2-difluorobenzene, 28% by mole of 4-(trans-4-(trans-4-n-propylcyclohexyl) cyclohexyl)-1,2-difluorobenzene, and 20% by mole of 4-(trans-4-(trans-4-n-pentylcyclohexyl) cyclohexyl), 2-difluorobenzene. The mixture had the following phase transition temperatures.

$T_{NI}$ (nematic phase-isotropic phase transition temperature) =75° C.

$T_{CN}$ (crystal phase phase-nematic phase transition temperature)=0.5° C.

80% by mole of the mixture was further mixed with 15% by mole of (4(4-n-propyl-4-silacylohexyl)phenyl) trans-3,4-difluorobenzoate obtained in Example 32. The resultant mixture exhibited a nematic-isotropic phase transition temperature shifted to a higher temperature side as shown below.

$T_{NI}$ (nematic phase-isotropic phase transition temperature) =80.5° C.

$T_{CN}$ (crystal phase-nematic phase transition temperature)= 1.5° C.

As will be apparent from the foregoing examples, the novel compounds of the invention exhibit relatively high $T_{NI}$ (nematic-isotropic phase transition temperature) without any significant increase in viscosity of the mixed liquid crystal compositions comprising the novel compounds which have a silicon atom in the molecule. Since the $T_{NI}$ is high, the liquid crystal composition can work at a higher temperature and can be used in various fields such as of on-vehicle liquid crystal panels.

What is claimed is:

1. A silacyclohexane compound of the following formula (I)

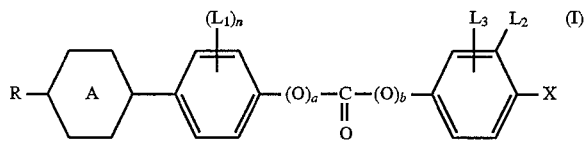

wherein R represents a linear alkyl group having from 1 to 10 carbon atoms, a branched alkyl group having from 3 to 8 carbon atoms, an alkoxyalkyl group having from 2 to 7 carbon atoms, a mono or difluoroalkyl group having from 1 to 10 carbon atoms or an alkenyl group having from 2 to 8 carbon atoms;

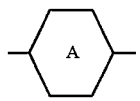

represents a trans-1-sila-1,4-cyclohexylene group or trans-4-sila-1,4-cyclohexylene group in which the silicon atom at the 1 or 4 position has a substituent of H, F, Cl or $CH_3$; $L_1$ represents F, $L_2$ and $L_3$ independently represent H, F, Cl or $CH_3$; X represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_3Cl$, $OCHFCl$, $OCHF_2$, $(O)_tCY=CX_1X_2$ wherein 1 is 0 or 1, Y and X1 independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl and n is a n integer of 0, 1, or 2 and a and b are, respectively, 0 or 1 provided that it a+b=1.

2. A silacyclohexane compound according to claim 1, wherein said compound is of the general formula (II)

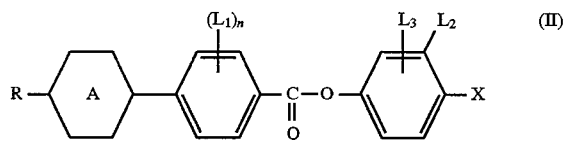

wherein R, X, $L_1$, $L_2$, L3, n and

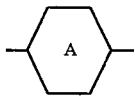

are as defined in claim 1, respectively.

3. A silacyclohexane compound according to claim 2, wherein said compound is of the following formula (IV)

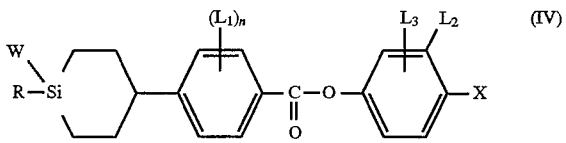

wherein R, X, $L_1$, L2, $L_3$ and n are as defined in claim 1, repsectively, and W represents H, F, Cl or $CH_3$.

4. A silacyclohexane compound according to claim 2, wherein said compound is of the following formula (V)

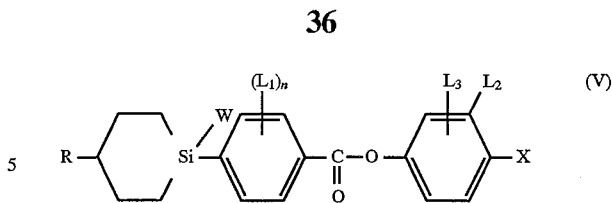

wherein R, X, $L_1$, $L_2$, $L_3$ and n are as defined in claim 1, respectively, and W represents H, F, Cl or $CH_3$.

5. A silacyclohexane compound according to claim 1, wherein said compound is of the following formula (III)

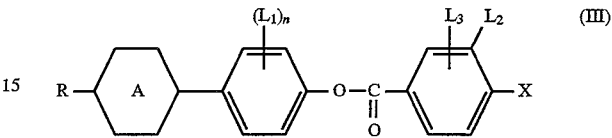

wherein R, X, $L_1$, $L_2$, $L_3$, n and

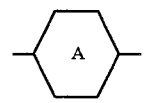

are as defined in claim 1, respectively.

6. A silacyclohexane compound according to claim 5, wherein said compound is of the following formula (VI)

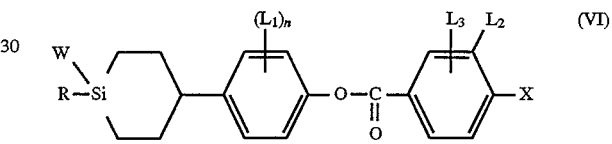

wherein R, X, $L_1$, $L_2$, $L_3$ and n are as defined in claim 1, repsectively, and W represents H, F, Cl or $CH_3$.

7. A silacyclohexane compound according to claim 5, wherein said compound is of the following formula (VII)

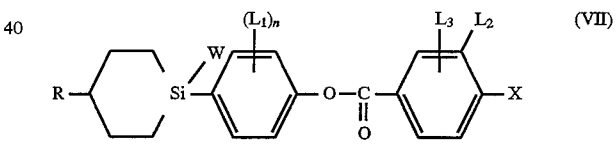

wherein R, X, $L_1$, $L_2$, $L_3$ and n are as defined in claim 1, repsectively, and W represents H, F, Cl or $CH_3$.

8. A liquid crystal composition comprising at least one silacyclohexane compound of the following formula (I)

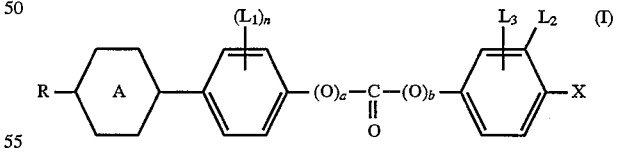

wherein R, X, $L_1$, $L_2$, $L_3$, n, a, b and

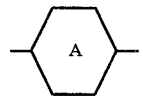

are, respectively, as defined in claim 1.

9. A liquid crystal composition according to claim 8, wherein said at least one silacyclohexane compound is present in an amount of from 1 to 50% by mole based on said composition.

10. A liquid crystal composition according to claim 8, further comprising at least one compound selected from the group consisring of compounds of the following formulas

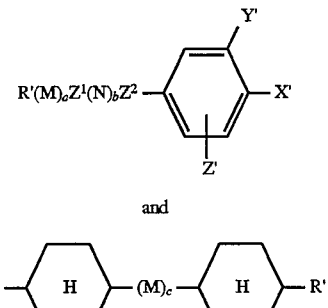

and wherein each R' represents a linear alkyl group having from 1 to 10 carbon atoms, a branched alkyl group having from 3 to 8 carbon atoms, a mono or difluoroalkyl group having from 1 to 10 carbon atoms, an alkoxyalkyl group having from 2 to 7 carbon atoms or an alkenyl group having from 2 to 8 carbon atoms as defined in the afore-indicated formula (I); X' represents a linear alkyl group having from 1 to 10 carbon atoms, a linear alkoxy group having from 1 to 10 carbon atoms, an alkoxyalkyl group having from 2 to 7 carbon atoms, CN, F, Cl, $CF_3$, $CF_2Cl$, $CHFCl$, $OCF_3$, $OCF_2Cl$, $OCHFCl$, $OCHF_2$, $(O)_lCY=CX_1X_2$ wherein l is 0 or 1, Y and $X_1$ independently represent H, F or Cl, $X_2$ represents F or Cl, or $O(CH_2)_r(CF_2)_sX_3$ wherein r and s are, respectively, 0, 1 or 2 provided that r+s=2, 3 or 4, $X_3$ represents H, F or Cl; Y' and Z' independently represent H or F; M and N independently represent (1) an unsubstituted or substituted with one or more radicals selected from the group consisring of F, Cl, Br, CN and an alkyl group having from one to three carbon atoms trans-1,4-cyclohexylene group, (2) a trans-1,4-cyclohexylene group wherein one $CH_2$ unit or two $CH_2$ units, which are not adjacent to each other, of the cyclohexane ring are replaced by O or S, (3) a 1,4-cyclohexenylene group, (4) an unsubstituted or substituted with one or two radicals selected from the group consisring of F, Cl, $CH_3$ and CN groups 1,4-phenylene group and (5) a 1,4-phenylene group in which one or two CH units of the phenylene group are replaced by nitrogen atom, a and b are, respectively, 0, 1 or 2 provided that a+b=1,2 or 3, and c is 0, 1 or 2; and $Z^1$ and $Z^2$ are, respectively, $-CH_2CH_2-$, $-CH=CH-$, $-C\equiv C-$, $-CO_2-$, $-OCO-$, $-CH_2O-$, $-OCH_2-$ or single bond.

11. A liquid crystal display device comprising the composition defined in claim 8.

* * * * *